(12) United States Patent
Roy et al.

(10) Patent No.: US 9,757,487 B2
(45) Date of Patent: Sep. 12, 2017

(54) SELF-STERILIZING DEVICE USING PLASMA FIELDS

(75) Inventors: Subrata Roy, Gainesville, FL (US); Karl Zawoy, High Springs, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 616 days.

(21) Appl. No.: 12/743,625

(22) PCT Filed: Nov. 21, 2008

(86) PCT No.: PCT/US2008/084378
§ 371 (c)(1),
(2), (4) Date: Oct. 1, 2010

(87) PCT Pub. No.: WO2009/067682
PCT Pub. Date: May 28, 2009

(65) Prior Publication Data
US 2011/0116967 A1    May 19, 2011

Related U.S. Application Data

(60) Provisional application No. 60/989,496, filed on Nov. 21, 2007.

(51) Int. Cl.
*A61L 2/00*   (2006.01)
*A61L 2/14*   (2006.01)
(Continued)

(52) U.S. Cl.
CPC ...... *A61L 2/14* (2013.01); *A61L 2/24* (2013.01); *A61L 2202/11* (2013.01); *A61L 2202/24* (2013.01)

(58) Field of Classification Search
CPC ............... A61L 2/14; A61L 2202/11
(Continued)

(56) References Cited

U.S. PATENT DOCUMENTS 3,434,476 A   3/1969   Shaw et al.
4,818,488 A   4/1989   Jacob
(Continued)

FOREIGN PATENT DOCUMENTS

CN   1243013 A     2/2000
CN   101259036 A   9/2008
(Continued)

OTHER PUBLICATIONS

Akan, T., et al., "Plasma Sterilization Using the High Voltage Pulsed Discharge at Atmospheric Pressure," *Journal of Applied Sciences*, Jul. 2006, pp. 1566-1570, vol. 6, No. 7.
(Continued)

*Primary Examiner* — Kevin Joyner
(74) *Attorney, Agent, or Firm* — Saliwanchik, Lloyd & Eisenschenk

(57) ABSTRACT

Embodiments of the invention relate to a method and apparatus for self-sterilizing a surface or other portion of the apparatus and/or sterilizing other objects. Embodiments can utilize self-generated and/or remotely controlled plasma fields for the purpose of self-sterilization and/or sterilization of another object. Embodiments of the invention can have broad applications in procedures and equipment requiring the sterility of devices used for medical procedures, decontamination procedures, drug delivery, sterility of consumer products, and sterility of food preparation equipment and tools.

74 Claims, 10 Drawing Sheets

(51) Int. Cl.
A61L 2/24 (2006.01)
B01J 19/08 (2006.01)

(58) Field of Classification Search
USPC .............................................. 422/22, 186.05
See application file for complete search history.

(56) References Cited

U.S. PATENT DOCUMENTS

| | | | |
|---|---|---|---|
| 4,931,261 | A | 6/1990 | Jacob |
| 5,451,368 | A | 9/1995 | Jacob |
| 5,667,753 | A | 9/1997 | Jacobs et al. |
| 5,876,666 | A | 3/1999 | Lin et al. |
| 6,037,562 | A | 3/2000 | Awakowicz et al. |
| 6,730,238 | B2 | 5/2004 | Li et al. |
| 6,767,509 | B1 | 7/2004 | Griesbach et al. |
| 7,261,852 | B2 | 8/2007 | Rinzler et al. |
| 7,799,290 | B2 * | 9/2010 | Hammerstrom et al. .................. 422/186.04 |
| 2004/0037756 | A1 | 2/2004 | Houston, Jr. et al. |
| 2004/0140194 | A1 * | 7/2004 | Taylor et al. ................ 204/164 |
| 2005/0179395 | A1 * | 8/2005 | Pai ........................... 315/111.21 |
| 2005/0269199 | A1 | 12/2005 | Pollak et al. |
| 2006/0022606 | A1 | 2/2006 | DeVries et al. |
| 2006/0244386 | A1 | 11/2006 | Hooke et al. |
| 2006/0257280 | A1 * | 11/2006 | Hammerstrom et al. ........ 422/4 |
| 2006/0272673 | A1 | 12/2006 | Kurunczi |
| 2007/0017636 | A1 * | 1/2007 | Goto et al. ............... 156/345.47 |
| 2008/0112846 | A1 | 5/2008 | Dieras et al. |
| 2008/0260578 | A1 * | 10/2008 | Engemann et al. ............ 422/56 |

FOREIGN PATENT DOCUMENTS

| | | |
|---|---|---|
| DE | 19819909 A | 11/1999 |
| EP | 1084713 A1 | 3/2001 |
| EP | 1726314 A1 | 11/2006 |
| JP | 2003-210556 | 7/2003 |
| JP | 2006-239230 A | 9/2006 |
| JP | 2007-234297 | 9/2007 |
| WO | WO-00-54819 A1 | 9/2000 |
| WO | WO-02-099836 A1 | 12/2002 |
| WO | WO-2006/039883 A1 | 4/2006 |
| WO | WO-2007-031250 A1 | 3/2007 |
| WO | WO-2007/032172 | 3/2007 |
| WO | WO-2007-067924 A2 | 6/2007 |

OTHER PUBLICATIONS

Alemskii, I.N., et al., "Electric Characteristics of a Surface Barrier Discharge with a Plasma Induction Electrode," *Plasma Physics Reports*, 2006, pp. 612-617, vol. 37, No. 7.

Choi, J.H., et al., "Analysis of Sterilization Effect by Pulsed Dielectric Barrier Discharge," *Journal of Electrostatics*, Jan. 2006, pp. 17-22, vol. 64, No. 1.

Fridman, G., et al., "Bio-Medical Applications of Non-Thermal Atmospheric Pressure Plasma," 37th AIAA Plasma Dynamics and Lasers Conference, Jun. 5-8, 2006.

Fridman, G., et al., "Comparison of Direct and Indirect Effects of Non-Thermal Atmospheric-Pressure Plasma on Bacteria," *Plasma Processes and Polymers*, May 2007, pp. 370-375, vol. 4, No. 4.

Fridman, G., et al., "Use of Non-Thermal Atmospheric Pressure Plasma Discharge for Coagulation and Sterilization of Surface Wounds," 32nd IEEE International Conference on Plasma Science, Jun. 20-23, 2005, *IEEE Conference Record Abstracts*, p. 257.

Halfmann, H., et al., "A Double Inductively Coupled Plasma for Sterilization of Medical Devices," *Journal of Physics D: Applied Physics*, Jul. 2007, pp. 4145-4154, vol. 40, No. 14.

Heise, M., et al., "Sterilization of Polymer Foils with Dielectric Barrier Discharges at Atmospheric Pressue," *Plasmas and Polymers*, 2004, pp. 23-33, vol. 9, No. 1.

Kanazawa, S., et al., "Stable Glow Plasma at Atmospheric Pressure," *Journal of Physics D: Applied Physics*, 1988, pp. 838-840, vol. 21, No. 5.

Kanda, N., et al., "Atmospheric Pressure Glow Plasma and Its Application to Surface Treatment and Film Deposition," *Proceedings of the 10$^{th}$ Symposium on Plasma Chemistry*, 1991, vol. 3, Paper No. 3.2-20.

Laroussi, M., et al., "Plasma-Based Sterilization," 26$^{th}$ International Conference on Phenomena in Ionized Gases, Jul. 2003, Greifswald, Germany, Topic No. 14.

Laroussi, M., et al., "The Resistive Barrier Discharge," *IEEE Transactions on Plasma Science*, 2002, pp. 158-159, vol. 30, No. 1.

Lerouge, S., et al., "Plasma Sterilization: A Review of Parameters, Mechanisms, and Limitations," *Plasmas and Polymers*, Sep. 2001, pp. 175-188, vol. 6, No. 3.

Moisan, M., et al., "Low-Temperature Sterilization Using Gas Plasmas: A Review of the Experiments and an Analysis of the Inactivation Mechanisms," *International Journal of Pharmaceutics*, 2001, pp. 1-21, vol. 226, Nos. 1-2.

Nagatsu, M., et al., "Line-Shaped Dielectric Barrier Discharges for Inner Surface Processing of Tubular Medical Instruments," 28$^{th}$ International Conference on Phenomena in Ionized Gases, Jul. 2007, Prague, Czech Republic, Topic No. 16.

Roth, J.R., "Aerodynamic Flow Acceleration Using Paraelectric and Peristaltic Electrohydrodynamic Effects of a One Atmosphere Uniform Glow Discharge Plasma," *Physics of Plasmas*, 2003, pp. 2117-2126, vol. 10, No. 5.

Roy, S., et al., "Effective Discharge Dynamics for Plasma Actuators," 44$^{th}$ AIAA Aerospace Sciences Meeting and Exhibit, Jan. 2006, Reno, NV, Pub No. AIAA-2006-0374.

Roy, S., "Flow Actuation Using Radio Frequency in Partially-Ionized Collisional Plasmas," *Applied Physics Letters*, 2005, Article No. 101502, vol. 86, No. 10.

Schrader, C. et al., "Micro-Structured Electrode Arrays: Plasma Based Sterilization and Coating Over a Wide Pressure Range," *Surface & Coatings Technology*, 2005, pp. 655-659, vol. 200.

Schutze, A., et al., "The Atmospheric-Pressure Plasma Jet: A Review and Comparison to Other Plasma Sources," *IEEE Transactions on Plasma Science*, 1998, pp. 1685-1694, vol. 26, No. 6.

Tien, L.C., et al., "ZnO Nanowires for Sensing and Device Applications," 212th Electrochemical Society Meeting, Oct. 7-12, 2007, Abstract No. 1195.

Tanino, M., etal., "Sterilization Using Dielectric Barrier Discharge at Atmospheric Pressure," 40th Industry Applications Society Annual Meeting, 2005, Conference Record, pp. 784-788, vol. 2.

\* cited by examiner

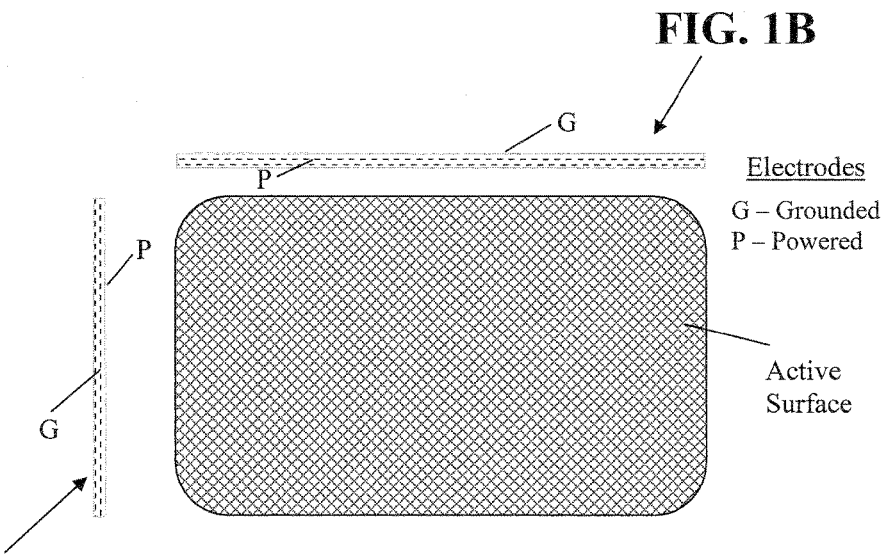
FIG. 1B
FIG. 1A
FIG. 1C
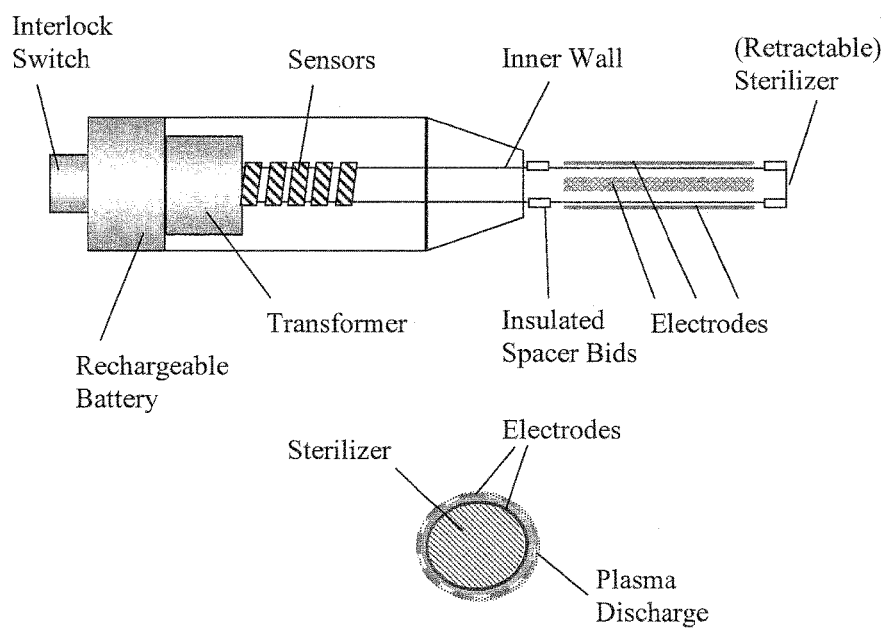
FIG. 2

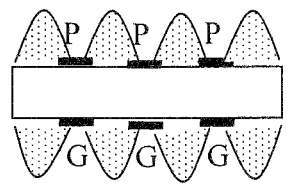
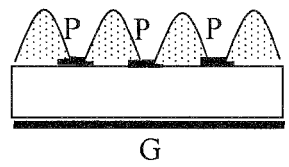
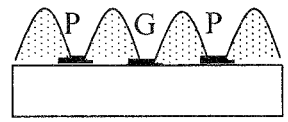
FIG. 9A  FIG. 9B  FIG. 9C
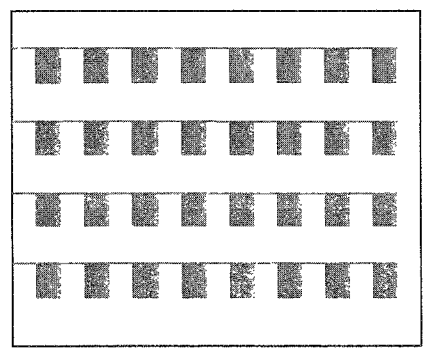
FIG. 9D
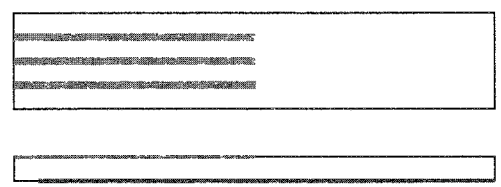
FIG. 9E

Before 100 μl  After 1 min

Before 10 μl  After 1 min

SELF-STERILIZING DEVICE USING PLASMA FIELDS

CROSS-REFERENCE TO RELATED APPLICATION APPLICATIONS

This application is the U.S. national stage application of International Patent Application No. PCT/US2008/084378, filed Nov. 21, 2008, which claims the benefit of U.S. Provisional Application Ser. No. 60/989,496, filed Nov. 21, 2007, the disclosures of which are hereby incorporated by reference in its their entireties, including any figures, tables, or drawings.

BACKGROUND OF INVENTION

The generation of plasma due to electrical input has been studied both experimentally and theoretically in recent years [see references 1-4]. The basic mechanisms inherent in non-equilibrium discharges such as obtained through DC, RF, or microwave excitation have also been utilized for ionization purposes, so as to increase the conductivity of air for further control with ponderomotive forces generated with an imposed magnetic field. Dielectric barrier discharge (DBD) involves one dielectric coated electrode that is typically exposed at the surface to the surrounding atmosphere, while another electrode is embedded inside a layer of insulator. The emission of UV light as well as chemical processes in surface plasmas is suitable for decontamination in a short timescale and using very low power and heat [see references 5, 6].

It has been found [see reference 5] that with special DBD arrangements, a fast reduction of cells by more than four orders of magnitude is possible within a few seconds, even for UV resistant cells. Moisan et al. [see reference 7] have observed that in contrast to classical sterilization where the survival curves of microorganisms under UV irradiation show a unique linear decay, plasma sterilization yields survival diagrams that show three basic mechanisms. First, a rapid direct destruction by plasma related UV irradiation of the genetic material of microorganisms; second, a gradual erosion of the microorganisms due to intrinsic photodesorption to form volatile compounds intrinsic to the microorganisms; and third, erosion of the microorganisms due to etching from radicals formed due to plasma ionization. Together, plasma sterilization is much (order of magnitude) faster than the traditional sterilization process.

Traditionally, in plasma discharge, a DC voltage potential is placed across two electrodes. If the voltage potential is gradually increased, at the breakdown voltage $V_B$, the current and the amount of excitation of the neutral gas becomes large enough to produce a visible plasma. According to Paschen's law, the breakdown voltage for a particular gas depends on the product (p×d) of the gas pressure and the distance between the electrodes. For any gas there is unique p×d value referred to as the Stoletow point where volumetric ionization is the maximum. The Stoletow point for air requires a minimum $V_B$=360 V and p×d=5.7 Torr-mm.

Unfortunately near atmospheric pressure, the allowable electrode spacing necessary for maximum volumetric ionization is d=7.7 μm. In some applications, for example in high-speed air vehicles, this is an impractical limitation. A solution to this limitation comes from the recent development of RF glow discharge using an a.c. voltage potential across the electrodes. The frequency of the current must be such that within a period of the a.c. cycle, electrons must travel to the electrodes and generate a charge, while the heavier ions cannot. Based on reported experiments [see reference 2] in air or other gases at 760±25 torr, a homogeneous glow can be maintained at 3 to 20 kHz RF and inns electrode voltage between 2 to 15 kV. A critical criterion for such discharge in air is to meet the electric field requirement of about 30 kV/cm. While the voltage is high, only a few milliamps current is required to sustain a RF driven barrier discharge.

BRIEF SUMMARY

Embodiments of the invention relate to a method and apparatus for self-sterilizing or self-decontaminating a surface or other portion of the apparatus and/or sterilizing or decontaminating other objects. Embodiments can utilize self-generated and/or remotely controlled plasma fields for the purpose of self-sterilization and/or sterilization of another object. Embodiments of the invention can have broad applications in procedures and equipment requiring the sterility of devices used for decontamination, medical procedures, drug delivery, sterility of consumer products, and sterility of food preparation equipment and tools. Various embodiments of the invention can involve eliminating or greatly reducing foreign materials on a surface of the device, or other surface, through the use of a plasma field generated by the device. In certain embodiments, matter on or near a surface, such as living organisms, tissue, germs, bacteria, pathogens, biological agents, viruses, metabolically inert agents, pyrons, organism matter, and microorganisms, can be killed and/or vaporized from the surface, and/or non-living materials, such as chemical agents or other types of potentially harmful materials can be vaporized or otherwise rendered less harmful. Plasma field generation may also include the generation of ionized air, radicals, photons, and/or ultraviolet light. Specific embodiments are also capable of sensing the surface or environment to determine if the surface is potentially contaminated, contaminated, and/or not sterile.

BRIEF DESCRIPTION OF DRAWINGS

FIGS. 1A-1C show a flat flexible self-sterilizing laminate surface in accordance with an embodiment of the invention.

FIG. 2 shows an embodiment of a self-sterilization device incorporating a rollable surface that can be utilized to sterilize other objects.

FIG. 8 shows an embodiment of a self-sterilizing structure having a plurality of apertures there through.

FIGS. 9A-9F show various electrode layouts that allow self-sterilization of a surface.

DETAILED DISCLOSURE

Embodiments of the invention relate to a method and apparatus for self-sterilizing a surface or other portion of the apparatus and/or sterilizing other objects. Embodiments can utilize self-generated and/or remotely controlled plasma fields for the purpose of self-sterilization and/or sterilization of another object. Embodiments of the invention can have broad applications in procedures and equipment requiring devices for decontamination, medical procedures, drug delivery, sterility of consumer products, and sterility of food preparation equipment and tools. The sterilization and/or decontamination can reduce or eliminate, for example, pathogens, bacteria, chemical agents, biological agents, or other materials. The plasma can change the chemical structure and can gasify materials on the surface.

In specific embodiments of the invention, surfaces can be sterilized in accordance with appropriate International Organization for Sterilization (ISO) standards. Examples of ISO standards that can be met by embodiments of the subject invention include, but are not limited to, ISO 17664:2004—Sterilization of medical devices—Information to be provided by the manufacturer for the processing of resterilizable medical devices, ISO 11138—4:2006—Sterilization of health care products—Biological indicators, ISO 11737—2:1998—Sterilization of medical devices—Microbiological methods—Part 2: Tests of sterility performed in the validation of a sterilization process, ISO 14161:2000—Sterilization of health care products—Biological indicators—Guidance for the selection, use and interpretation of results, ISO 14937:2000—Sterilization of health care products—General requirements for characterization of a sterilizing agent and the development, validation and routine control of a sterilization process for medical devices, ISO 11737—1:2006—Sterilization of medical devices—Microbiological methods—Part 1: Determination of a population of microorganisms on products. In addition, various embodiments can meet the standard provided in Seymour S Block. 2000 Disinfection, Sterilization, and Preservation 5$^{th}$ ed. Lippencott, Williams, and Wilkens.

Figure 9F:
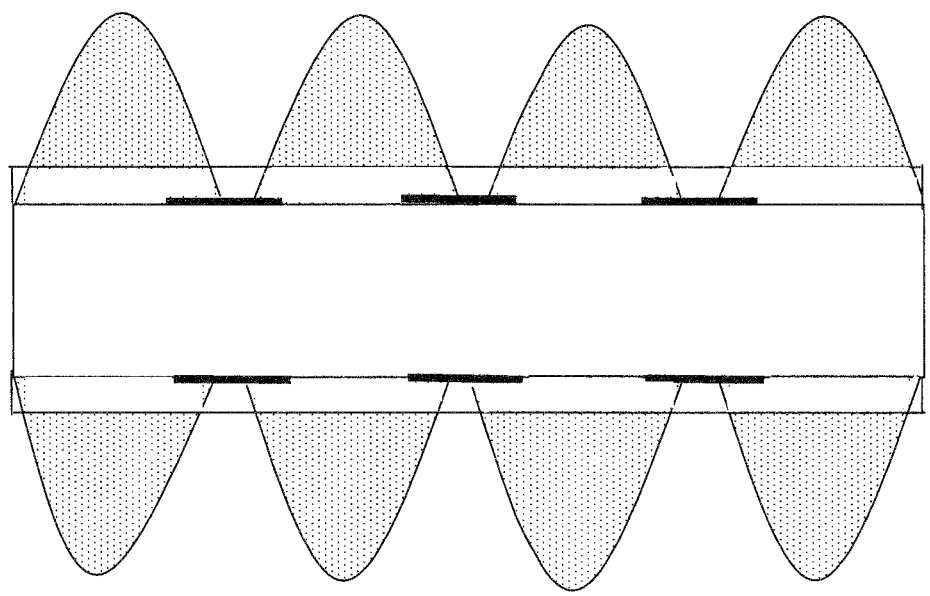

Embodiments can incorporate electrode structures for providing sterilizing plasmas into a variety of surfaces that can be self-sterilized. Surfaces having a variety of shapes can be incorporated with embodiments of the invention. A flat laminate surface can be used with, for example, a cutting board, a surgical surface, or a scalpel and can incorporate an array of embedded electrodes for producing an appropriate plasma. In a specific embodiment, a voltage between 2-20 kV can be applied across electrodes. In another specific embodiment, a peak-to-peak ac voltage of 2-20 kV can be applied, and in a more specific embodiment the ac voltage is 1-50 kHz RF voltage. FIGS. 1A-C show an embodiment of a flat, flexible, self-sterilizing laminate surface, with cross-sectional views (FIGS. 1B and 1C) of the laminate surface. The laminate surface can have a dielectric layer positioned in between two electrode layers. Referring to FIGS. 1A-1C, a layer of ground electrodes are positioned apart from a layer of powered electrodes. The powered electrodes and the ground electrodes form a crossing pattern. Driving the powered electrodes with a voltage relative to the grounded electrodes produces a plasma that sterilizes and/or decontaminates the active surface. The electrodes can have a variety of shapes and sizes. FIG. 9A shows an electrode pattern that is shifted when compared to the embodiment shown in FIGS. 1A-1C; while FIGS. 9B and 9C show other electrode configurations that can be used with the surface of FIGS. 1A-1C, where FIG. 9B shows the use of a ground plate. Other electrode configurations can also be used. In various embodiments, the electrodes can be exposed to the environment in contact with the surface, the electrodes can be embedded in the surface, the electrodes can have a layer of material, such as hydrophobic thin insulating layer, TEFLON™, or a dielectric material layer between the electrode and the environment, or the electrodes can be structured as a combination of exposed, embedded, and covered. FIG. 9F shows an embodiment with a coating over the electrodes such that the electrodes are not exposed to the environment. The outer surface of the coating can then be sterilized via the plasma generated by the electrodes via electric fields penetrating the coating.

In a further embodiment, a surface like the surface shown in FIGS. 1A-1C, can sterilize itself as well as sterilize specific objects placed on the surface. In this way, an embodiment of the invention can include a plate, or other structure having a self-sterilizing surface, and one or more objects sized and made of appropriate material to be placed on the plate such that the objects can also be sterilized. The plate can have structures, such as indentations or extended portions, that facilitate positioning the object and/or enabling the plasma generated to sterilize the objects placed on the plate. There can be specific settings to sterilize the plate, to sterilize a first number and/or type of object and to sterilize a second number and/or type of object, where the settings can have, for example, different powers and/or durations. An example of such an embodiment is a surgical plate and a variety of surgical instruments. Such sterilization or decontamination can occur automatically without user intervention, or by way of user input. In a further specific embodiment, referring to FIG. 2, sensors can be incorporated on the retractable portion of the sterilizer that can detect matter that needs to be sterilized. The sensors upon detection of such material, can cause the sterilizer to turn on the plasma to sterilize the surface the matter is detected on. In this way, the plasma need not be on all the time.

FIG. 2 shows an embodiment of a device that can sterilize a surface separate from the device by rolling over the separate surface, so as to provide a plasma over the device surface that can roll over other surfaces. As shown in FIG. 2, electrodes can be incorporated into an outer cylindrical surface that can roll over other surfaces. Again, the electrodes can be positioned on the surface, embedded into the surface, exposed to the environment, or have a coating between electrode and the environment. An interlock switch can act to push the retractable sterilizer out of the device body and retract the retractable sterilizer back into the device body. Other applications for the use of electrodes on outer cylindrical surfaces include, but are not limited to, scopes or probes, diagnostic surfaces, and laboratory testing equipment. The interlock can protect inadvertent exposure from the plasma field. The insulated spacers shown in FIG. 2 can allow the outer surface of the cylindrical retractable sterilizer to be located proximate a surface to be sterilized and/or decontaminated with touching the surface. The use of the spacers can allow the separation between the surface of the sterilizer and the surface to be sterilized and/or decontaminated to be controlled. In the cross-section of the cylindrical portion of the sterilizer shown in FIG. 2, the inner electrode is shown as a continuous hollow cylindrical and the outer electrodes are shown as longitudinal strips, separated from the inner electrode by an insulating material, such as a dielectric material. Other electrode shapes can be used with the device of FIG. 2, including, but not limited to, longitudinal strips for the inner electrode, ring electrodes spaced longitudinally for the outer and/or inner electrodes, or other combinations. The interior of the cylindrical portion of the sterilizer can be hollow or filled with one or more materials.

Figure 3:
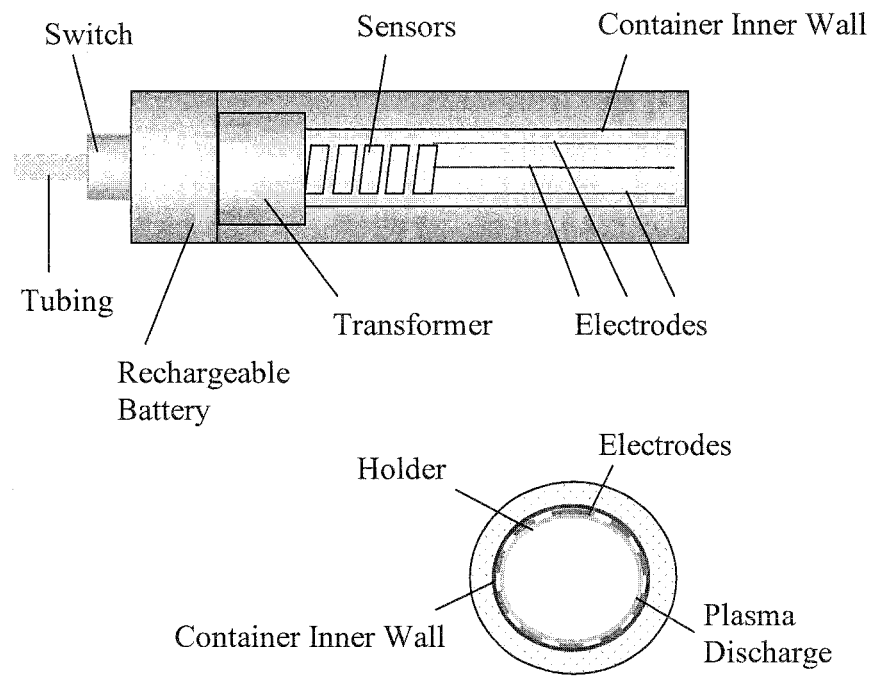
FIG. 3 shows an embodiment of a self-sterilization container.

As shown in FIG. 3, electrodes can be incorporated into an inner cylindrical surface. Other applications for the use of electrodes on inner cylindrical surfaces include, but are not limited to, drug delivery ports, beakers, flasks, and laboratory pipettes. The switch can be used to turn on and off the electrodes. In an embodiment, the electrodes can be embedded in the inner surface of the container. In a specific embodiment, a fluid can be brought in through the tubing. The tubing can allow entry of an electrical connection, blood, IV drugs, or other materials. The electrodes are shown on the container inner surface, but could extend over the lip and/or the outer surface as well. The bottom of the container can also incorporate electrodes. The container can have many cross-sectional shapes, such as rectangular. In a specific embodiment, the electrodes incorporated into the inner cylindrical surface can provide a discharge that extends sufficiently above a surface, such that the electrodes create a plasma to, for example, sterilize a fluid, such as air, flowing through the cylinder. As discussed with respect to the embodiment of FIG. 2, the electrode can have a variety of configurations and shapes.

Figure 4:
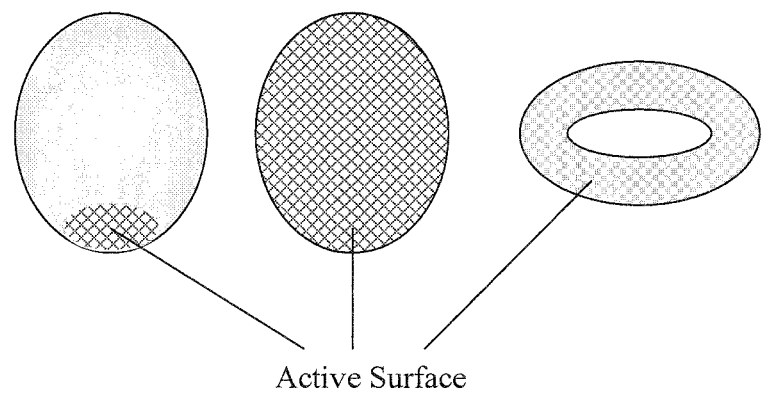
FIG. 4 shows various shapes of self-sterilization surfaces with various portions of surfaces performing active sterilization, in accordance with an embodiment of the invention.

As shown in FIG. 4, electrodes can be incorporated into spherical, doughnut, or other curved shaped surfaces for use in, for example, implantable diagnostic probes and/or laboratory probes that need to be sterilized between tests or samples. In an embodiment, a spherical surface can roll on another surface to sterilize the other surface.

Figure 5:
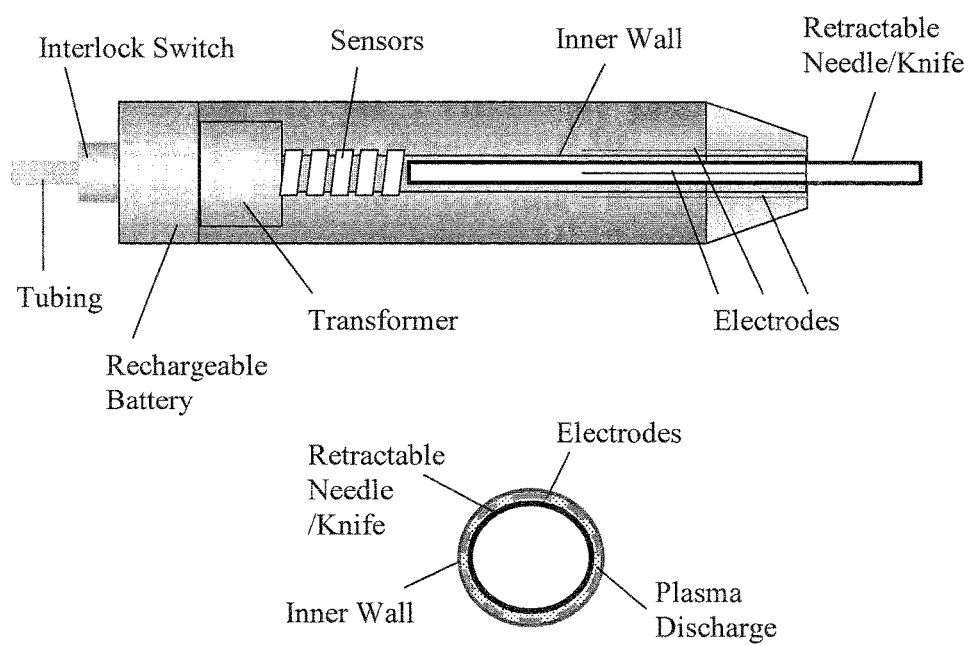
FIG. 5 shows an embodiment of a retractable self-sterilization device in accordance with the invention.

As shown in FIG. 5, electrodes can be incorporated into a device such that the electrodes can be positioned to produce a plasma so as to sterilize a needle shaft and tip or scalpel. In an embodiment, the electrodes in FIG. 5 can reside near the inner wall of the interior of the device with the needle or knife retracting into the interior of the device for sterilization. Alternatively, the electrodes can be designed to extend out of the interior of the device to sterilize the needle or knife and the electrodes can then retract into the interior of the device after sterilization.

In an alternative embodiment, one or more first electrodes can be positioned on the needle shaft, or other object to be sterilized, and one or more second electrodes can be positioned on the inner wall, or other position on the body section into which the needle retracts. A voltage can then be applied between the first and second electrodes to create a plasma to sterilize the needle and/or inner wall. The spacing between the needle and the inner wall can be controlled to control the plasma appropriately. In a further embodiment, electrodes can be extended into the needle, or other object and create plasma via the electrodes inserted into the needle or by applying a voltage from the electrodes inserted into the needle to electrodes on the inside surface of the needle.

The device shown in FIG. 5 can be used with, for example, IV needles, hypodermic needles, other needles used for medical procedures, diagnostic catheters, implantable devices, and scalpels. A specific embodiment is directed to an IV Cannula that self-sterilizes before insertion into patient and after it is removed from patient to minimize contamination or accidental infection to the patient or care-giver. The embodiment shown in FIG. 5 can be incorporated with medical devices such as a scalpel, syringe, catheter, electrode or other device that can self-sterilize during a medical procedure. For example, the scalpel can self-sterilize during use to alleviate cross-contamination between the infected and healthy part of the patients body or between patients. Typical usage is in triage or emergency situations or where there is a limited supply of medical devices or instruments. In specific embodiments, tolerances from sub-millimeter up to a millimeter between the needle or scalpel and the inner wall may be implemented. The electrode configurations can be similar to those discussed with respect to the embodiment of FIG. 3, as shown in the cross-section in FIG. 5, which also shows a retractable needle. A variety of electrode configurations can be used in accordance with the invention to accomplish the sterilization and/or decontamination. As an example, a portion of the inner wall can have electrodes and can be rotated around the needle, or the needle can be rotated to pass by the electrodes, to sterilize the entire needle surface. Likewise, a longitudinal portion of the inner wall can incorporate electrodes and the needle can be sterilized as it passes by the electrodes while being retracted or extended.

Figure 6A:
FIG. 6A shows an embodiment of a self-sterilizing braided tube.
Figure 6B:
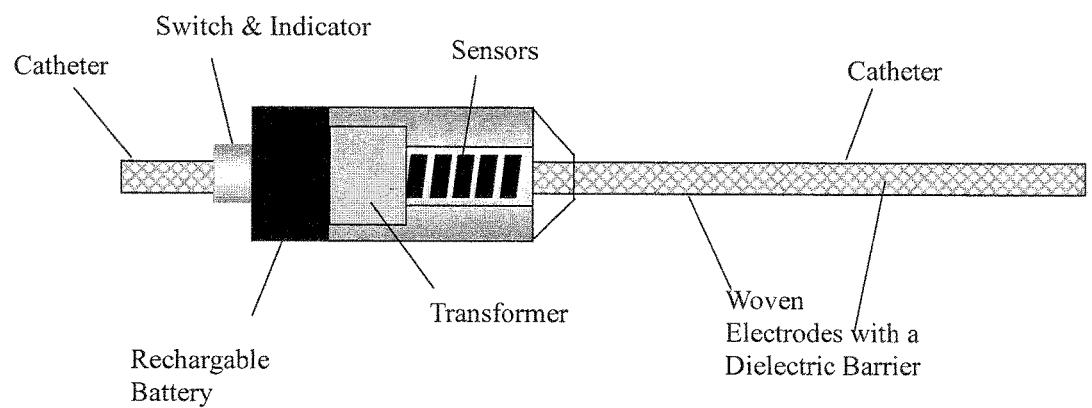
FIG. 6B shows an embodiment of a catheter incorporating the braided tube of FIG. 6A.

FIG. 6A shows an embodiment having a braided electrode incorporated into a tube, where a plasma can sterilize the inside surface of the tube, the outside surface of the tube, an object positioned around the tube, and/or an object inserted into the tube. Additional embodiments can be directed to a rod, such as a solid rod, that incorporates braided electrodes on the outer surface of the rod, or electrodes built into the outer surface of the rod, where the electrodes can have a variety of configurations including electrodes extending along the longitudinal axis of the rod, electrodes forming rings around the rod and/or other electrode orientations. Embodiments that can incorporate the tube of FIG. 6A include, but are not limited to, balloon catheters, urinary catheters, guiding catheters, ablation devices, and implantable/stent devices. Other non-medical applications can also incorporate the tube of FIG. 6A. A specific embodiment of a catheter incorporating the tube of FIG. 6A is shown in FIG. 6B. The braiding is used as a conductive pathway for generating plasma while also allowing the tube to bend without kinking. In a specific embodiment, medical devices are provided that can self-sterilize in a specific area or zone of the device to allow the continuous administration of drugs or treatments while maintaining a sterile barrier to the patient or care-giver. Other electrode structures can be utilized as well. The tube can have a plastic layer with wire electrodes braided around the inside and/or outside of the tube so as to leave spaces between the wire electrodes or otherwise prevent contact of adjacent wire electrodes. With one braid, the cross-hatching wire electrodes can be opposite electrodes. Some wire electrodes can be dielectrics to keep metal electrodes from touching. Again, a variety of electrode configurations and/or shapes can be used with the tube.

Figure 7:
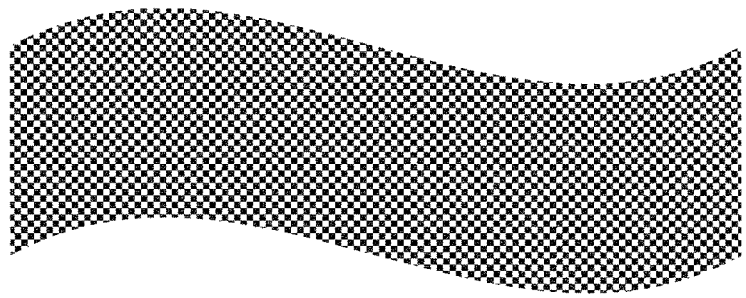
FIG. 7 shows an embodiment of a self-sterilizing cloth.

FIG. 7 shows a cloth or woven surface incorporating electrodes to clean or protect a device, patient, or any surface that needs a sterile barrier. The cloth or woven surface can be placed adjacent to surfaces and/or portions of items to be sterilized, and the plasma generated by the cloth or woven surface can sterilize such surfaces and/or portions of items. In such embodiments, regarding current ranges, it is desirable to minimize the currents. In an embodiment, the basic fabric or surface can be an insulating material such as TEFLON™. The embodiment shown in FIG. 7, as well as the embodiments shown in FIGS. 1A-1C, 4, and 6A-6B can be incorporated with medical devices that can self-sterilize in a specific area or zone on the device to minimize the buildup of surface contaminants, proteins, collagen, scar tissue or other materials to extend the operation, safety and efficacy of the device.

Figure 8:
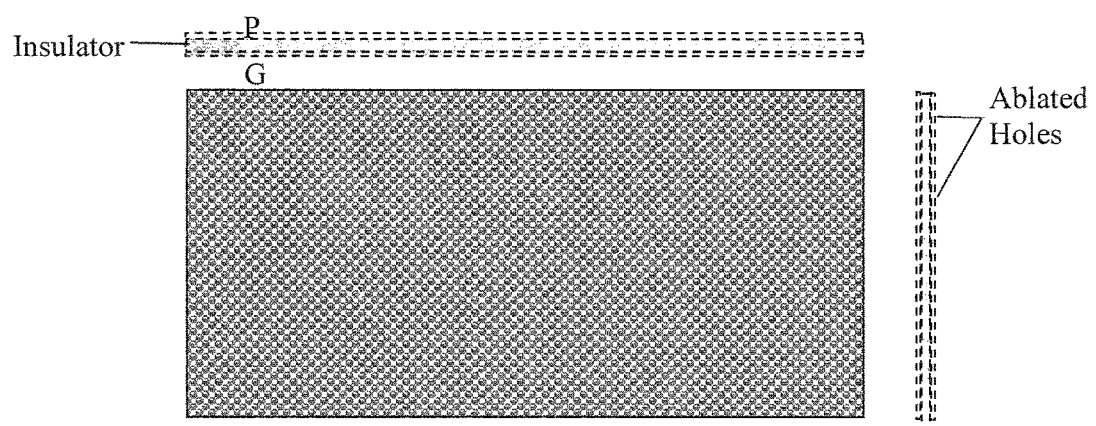

Referring to FIG. 8, a surface similar to a LCD television or computer display or a plasma television display can have an active surface composed of a matrix of individual pixilated electrode pairs. A pixel shaped electrode matrix, with appropriate addressing through a backplane, can be used. The pixel electrodes can have a variety of shapes. The pixel electrodes can have cross sectional diameters, or lateral dimensions, in the range of 1 µm to 100 µm or, even more preferably, in the range of 1 µm to 10 µm, and can be, for example, printed out or manufactured in manner similar to existing television and computer displays. In such embodiments regarding current ranges, it can be desirable to minimize the currents. FIG. 9D shows the top of a surface having pixilated electrodes. In the embodiment shown in FIG. 9D, each row of electrodes is driven by a sample input. In other embodiments, each pixel can be individually addressed, or the pixels can be grouped to meet the needs of the situation. Although ground plane is used in the embodiment of FIG. 9D, other electrode structures can be used for the electrode away from plasma generation as well. FIG. 9E shows an embodiment with strip electrodes and a ground plane. The cross section shown in FIG. 9B can show the cross section of FIG. 9E. FIG. 9F shows an embodiment having coating over the electrodes. The coating on the bottom of FIG. 9F allows plasma to be created on the bottom. Alternative embodiments can be used as insulating material for the coating on the bottom such that plasma would not be created on the bottom.

In a specific embodiment, referring to FIG. 8, ablation can be used to form the electrode shapes and/or patterns. Ablation, or other appropriate techniques can be used to form bores through the surface, from one side to another side, such that plasma can secrete within the bores by, for example, applying a voltage from the electrode on one side to the electrode on the other side. The plasma within the bores can sterilize and/or decontaminate a fluid flowing through the bores so as to purify the fluid. In this case, the surface of the bores can also be sterilized or decontaminated. Such bores can have cross-sectional dimensions on the order of a micron up to a mm, so as to allow the plasma to reach the entire cross-sectional flow of the fluid through the bores. In a specific embodiment, the diameter of cylindrical bores are less than 1 mm. In further embodiments, the diameter of the bores is in the range of 1 µm to 100 µm, or 1 µm to 1000 µm, at atmospheric pressure. Embodiments can be operated at pressures other than atmospheric.

Specific embodiments can involve the ability to control segments, or selected portions, of the surface that are sterilized or decontaminated by controlling which electrodes are activated. In a specific embodiment having a pixilated electrode structure, any combination of electrodes can be selected so as to control which areas of the surface are sterilized or decontaminated.

Power can be supplied to the electrodes in various embodiments of the invention by a variety of sources, including ac, dc, batteries, and wireless. Wireless power transfer can allow the device to have a coating over the entire body that seals the inside of the device from contamination from the environment.

Embodiments of the subject invention can incorporate electrodes having a variety of electrode structures, materials, and components. In specific embodiments, the electrodes can also be used as sensors. The active surface could be coated with a thin layer of polymer, glass or other dielectric material to provide an inert working surface for the user. Such coatings can also inhibit the formation of electrode corrosion and/or oxidation on the active surface. The coating used to provide an inert working surface can be coated with a conductive or semi-conductive material, such as carbon nanotubes, nanowires, conductive polymers and/or nanorods to enhance the generating of plasma on the coated surface.

Specific embodiments can incorporate the electrodes and electro-active components composed of any or all of the following: (1) electro-conductive polymers can be used in the construction of the device to control surface activation, channeling of plasma energy, perform localized or zone specific sterilization, and to lower the cost of manufacture; (2) transparent conducting films, such as, but not limited to, carbon nanotube films, surfaces coated with clusters of nanorods or nanowires, or surfaces coated with electro conductive polymers, can be used in the construction of the device, such as for sensors, to control surface activation, channeling of plasma energy, perform localized or zone specific sterilization, and to lower the cost of manufacture; and (3) material, described in (1) or (2), or polymers, doped with nanoparticles of silver, gold, copper, aluminum or other conductive or semi-conductive materials to act as sensors and/or to control surface activation, channeling of plasma energy, perform localized or zone specific sterilization, and to lower the cost of manufacture. The electrodes can be coated with a conductive or semi-conductive material such as carbon nanotubes, nanowires, conductive polymers and/or nanorods to enhance the generation of plasma. The dielectric barrier material onto, or into which, the electrodes are positioned that is exposed to the environment can be coated and/or include a conductive or semi-conductive material, such as carbon nanotubes, nanowires, conductive polymers and/or nanorods to enhance the generation of plasma.

Embodiments of the invention can operate with little, or no, interaction from a user and can sense contamination of the surface and/or potential contamination of the surface and self-sterilize or self-decontaminate the surface. Sensing potential contamination of the surface can be accomplished by sensing the physical environment of the surface, such as when the surface has been contacted or what materials are proximate the surface. As an example, the subject device can utilize a sensor capable of detecting anthrax, and when the sensor detects anthrax the device can sterilize or decontaminate all or portion of the surface, such as the portion of the surface most likely contaminated, or can sterilize or decontaminate a surface proximate the device surface, through the production of a plasma. The device can accomplish such actions automatically or can provide input to a user to allow the user to initiate the action.

The sensors used with specific embodiments can also be coated with a conductive or semi-conductive material, such as carbon nanotubes, nanowires, conductive polymers and/or nanorods to enhance sensor sensitivity and/or specificity. Likewise, any coating used to produce an inert working surface over the electrodes can be coated with a conductive or semi-conductive material, such as carbon nanotubes, nanowires, conductive polymers and/or nanorods to enhance sensor sensitivity and/or specificity.

The application of sterilization techniques in accordance with the subject invention is also suited for air cleaners, self-cleaning oven embodiments, bathroom door plates, door handles, cooking utensils, cutting boards, conveyor belts, storage containers, and handles for shopping carts. Also a HEPA-like filtration device with low power consumption can be achieved by incorporating the EHD micropump taught in international application no. PCT/US2008/071262, filed Jul. 25, 2008, not yet published, which is hereby incorporated by reference in its entirety, where the dust mite/microorganisms can be vaporized during their transit through the plasma excited active filtration membrane.

Each device can utilize electrodes, insulators, and electroactive components to create sterilizing plasmas. While the standard electrodes and insulating materials are reasonable for all ambient conditions, high temperature applications may be accommodated by appropriate choice of the dielectric (for example, glass-mica ceramic) and electrodes (for example, metallic perovskites). The plasma fields used to generate the self-sterilization process can be controlled by some or all of the variables listed in Table I.

TABLE I

| Variable | Typical Operation Range | Considerations |
|---|---|---|
| Voltage | 0.1 V-10 kV RMS, 10 V-10 kV RMS, or DC | |
| Current | µA-A | Device Specific |
| Pulse Frequency | 50 Hz-1 MHz or DC | |
| Distribution of electrodes | Top, bottom, outside or inside surface. | Device Specific |
| Ambient pressure | 0.1 mTorr-10 bars | Device Specific |
| Surface Exposure Time | Micro Seconds to Seconds based on electrode density and type of contamination | Device Specific |
| Surface Coating | Thin Polymer, glass or dielectric material | Device Specific |
| Electrode Placement | Number of Electrodes per unit area | Device Specific |
| Electrode Materials | Copper, platinum, and many alloys | Metals, conductive polymers, Nanotubes and Nanotube films |
| Conducting Materials | Copper, platinum, and alloys | Metals, conductive polymers, doped polymers, Nanotubes and Nanotube films, nanomaterials |
| Insulating Materials | TEFLON ™, PCB, FR4, and Ceramics | Plastics, doped polymers, Nanotubes and Nanotube films, nanomaterials |
| Ionizing Radiation | Atmospheric temperature and pressure | |

The plasma can be made continuous by using pulsed excitation of the electrodes in the range of 50 Hz to 10 MHz, and, in a specific embodiment, in the range of 0.1 kHz to 10 MHz. Direct current (DC) can also be used, such as pulsed DC. Specific embodiments can use a potential difference of 10V-50 kV, and, in a specific embodiment, 0.1V-10 kV DC. Plasma can be generated by exciting the adjacent electrodes in a phase controlled manner under ambient pressure ranging 0.1 mTorr-10 bars. Current levels from 1 µA to 1 A can be used in further specific embodiments and 1 µA to 100 A in further specific embodiments.

Various embodiments of the subject invention can improve the ability to minimize the transmission of infectious diseases of the blood, urine, saliva, or the spread of bacteria, viruses, cancer cells, pathogens or other forms of contamination. Embodiments can be incorporated in the food processing equipment and surfaces to minimize the growth of bacteria or other contaminants. Further embodiments, such as an adaptation of the embodiment shown in FIG. 7, can be used in air purification devices that have self-sterilizing plates or air filters used for respiratory care including: masks, hospital rooms, airplane air filtration, clean rooms, or involve air passing between, or through perforations in, surfaces such as shown in FIGS. 1A-1C. A mask can be fitted with self-sterilizing electrodes such that the mask can be worn and then self-sterilized when laid down.

Devices that can be applied to contaminated surface to sterilize them or provide a sterile barrier. A self-sterilizing electrode cloth, for example, as shown in FIG. 7, that can be wrapped around or cover laboratory diagnostic equipment in contact with the patient. After the procedure, the cloth is removed and then activated to self-sterilize and then reused for the next patient or procedure. An example of an application for various embodiments of the invention includes triage, where caregivers dealing with many injured people and going from person to person can use a device that can self-sterilize between patients. This can allow reuse of items that might otherwise be discarded or unusable until sterilization by a separate apparatus.

In various embodiments of the invention, plasmas can be generated for sterilization and/or decontamination via a variety of techniques. Such plasmas can be generated at atmospheric pressure, below atmospheric pressure, or above atmospheric pressure. Examples of such techniques include, but are not limited to, the dielectric barrier discharge (DBD) [See reference 12], the resistive barrier discharge (RBD) [See reference 13], and the atmospheric pressure plasma jet (APPJ) [See reference 14], all three references of which are incorporated herein in their entirety for the purposes of teaching how to generate the appropriate plasma. The RBD can be driven by DC or AC power sources, the DBD can operate at frequencies in the kHz range, and the APPJ can use a 13.56 MHz RF power source. These techniques can generate relatively large volumes of non-equilibrium, low temperature plasmas at or near atmospheric pressure. Specific embodiments produce plasmas having electron density in the range of $10^9$ cm$^{-3}$-$10^{11}$ cm$^{-3}$ and plasma power densities in the range of 10-300 mW/cm$^3$. In another specific embodiment, the plasma can be produced via floating electrode dielectric barrier discharge (FE-DBD).

Embodiments of the invention can include dielectric barrier discharge (DBD), where a first dielectric coated electrode, or set of electrodes, is exposed at the surface to the surrounding atmosphere (or covered with a coating) and a second electrode, or set of electrodes, is embedded inside a layer of insulator. Where a thin surface coating is in contact with the environment and plasma is generated by electrodes under the surface coating. A voltage can be applied between the first electrode, or set of electrodes, and the second electrode, or set of electrodes, to create a plasma at the surface. In order to disperse the plasma in a continuous fashion over the surface, phase lagged electrode circuitry may be employed. The phase lagged electrode circuitry applies voltages across corresponding electrodes from the first set of electrodes and the second set of electrodes, which form electrode pairs, such that different electrode pairs are excited with voltages having a phase lag compared with the voltage applied to the adjacent electrode pair. In an embodiment, the electrode spacing in each direction is such that the discharge is on both sides of the electrode. One set of electrodes may be powered with a pulsing a.c. or d.c. voltage and the other electrode set can be grounded. For a.c. voltage various waveforms can be utilized, such as sinusoidal, ramp, and sawtooth waveforms. The electrodes may also be operated at a beat frequency. In addition, application of fixed potential (d.c.) can be implemented.

Specific embodiments of electrode structures are shown in FIGS. 9A-9F. The electrode structures shown in FIGS. 9A-9F can also be driven with ac currents. The electrode spacing may vary from a few microns to several mm. The plasma exposure time required for self-sterilization may vary between a few microseconds to several milliseconds. For complete eradication of some organic substance exposure for several seconds may be necessary.

Referring to FIG. 8, an embodiment of the invention is shown. A laminate material having layers of electrodes, dielectrics, and sensors can be used to produce the embodiment shown in FIG. 8. A series of fine laser ablated holes or slots can be produced to create apertures through the laminate material. Equipotential surfaces, P and G, can be maintained at a voltage difference. An alternating or direct voltage may be applied across surfaces P and G. A plasma discharge can be generated through the holes and ejected outward in one or both directions. In this way, the surface can be self-sterilized on one or both surfaces. Insulator materials such as TEFLON™, PCB, FR4, and ceramics can be used in the laminate material to provide insulation between surfaces P and G. Electrode material such as copper, platinum, and alloys can be used as electrode materials for surfaces P and G. Selection of materials and the resulting surface tension can impact the selection of hole size.

Stretchable material can be used in order to control pore patterns. In an embodiment, the self-sterilizing laminate material can be incorporated with technology used in autoclaving equipment, gamma sterilization, sterile materials, chemicals, and/or processes that sterilize equipment and devices. In specific a embodiment, the self-sterilizing lamination material can be incorporated into, for example fabricated into, enclosures to be used in applications requiring autoclaving, gamma sterilization, or storage of sterile materials.

Various embodiments of the invention can incorporate one or more active surfaces, where an active surface of a self-sterilizing device can be in either a sterile state or a contaminated state, and the active surface can be re-sterilized by the device through the process of self-sterilization. The active surface can be used for a particular purpose, such as keeping a scalpel tip sterile. The sterile state of the active surface can be continuously or intermittently maintained by the device. Active surface self-sterilization can be initiated with or without the intervention of an end-user or other person, object, or external device. In embodiments, the self-sterilizing device is capable of sensing if the active surface has been contaminated or potentially contaminated. The self-sterilizing device can use sensors to determine the level of contamination and/or the possibility of contamination. Sensors can provide feedback on the state of the device before sterilization, during sterilization and/or after the sterilization cycle has occurred. Sensors can be used to provide feedback on the level of active surface contamination before sterilization, during sterilization, and/or after the sterilization cycle has occurred. Sterilization of the active surface can be initiated by the device with or without intervention by an end-user, other person, object, or external device. Contamination, or potential contamination, of information collected by the sensors can be one or more of the following: the location of contamination, such as a particular zone of the active surface; the duration of the contact that contaminated the active surface; other physical parameters associated with the contact, such as pressure, temperature, or movement on the active surface or movement of the self-sterilizing device.

A variety of sensor designs and placements can be used. In an embodiment, a sensor can be the plasma electrode or part of the plasma electrode operating in a sensing mode, instead of a sterilizing mode. An example of such a sensor includes a capacitive or continuity sensor. A sensor can be integrated with or located next to a plasma electrode. An example of such a sensor is a pressure sensor. A sensor can be located in proximity to the active surface, such as with an infrared curtain. A sensor can be located in the self-sterilizing device. An example of such a sensor is a start/stop switch and timer. Another example of such a sensor is an accelerometer to detect movement by the user. A sensor can be located at a remote location from the device. An example of a remotely located sensor is a sensor having a wireless link to a remote control location, such as a camera watching the device or a robot or device that enters a contaminated space and then self-sterilizes before or after leaving the contaminated space. Other sensor designs and placements can also be implemented in accordance with embodiments of the invention.

A variety of sensor types can be employed as well. Safety interlocks such as infrared curtains, capacitive lockout, or other means of detection during the sterilization cycle can be used for user/patient safety. The following are examples of sensors that could be used for sensing, feedback and control of the active surface or the device itself: infrared beam to provide a curtain over the active surface or device; radio frequency field to provide a curtain over the active surface or device; motion sensor to detect movement over the active surface or of the device; acoustic beam to detect movement over the active surface or of the device; temperature sensors to determine contact by another object or change in the device; pressure sensors to determine contact by another person or object or change in the device; capacitive sensors to determine contact by another person or object or change in the device; and conductivity sensors to determine contact by another person or object or change in the device. As an example, an infrared beam can be used to provide a curtain over the active surface to detect when the surface is touched and may, therefore, need sterilization, or to monitor build up on the active surface. As another example, an accelerometer can be used to detect movement of the device.

Example—Device State Diagram for Embodiment of a Self-Sterilizing Device

The following is a device state diagram for an embodiment of a self-sterilizing device in accordance with the subject invention. The device can indicate its state to a user through the use of a visual indicator such as red, yellow and/or green lights, or by a variety of other means such as a wireless signal to communicate with a Bluetooth enabled device.

| STEP | DEVICE STATE | COMMENT |
| --- | --- | --- |
| 1. | OFF | No Power to Device |
| 2. | ON | Power to Device |
| 3. | CALIBRATION | Self-Calibration Mode of Device and Sensors |
| 4. | SENSE ACTIVE SURFACE | Has the Device just been powered up (y/n)? Does Active Surface need to be re-sterilized (y/n)? |
| 5. | CHECK INTERLOCK (Open or Closed) | Is anything contacting the Active Surface (y/n)? OK to Proceed with Self-Sterilization of Active Surface (y/n)? |
| 6. | INTERLOCK OPEN | GOTO STAND-BY MODE Feedback State to User (see below) |

| STEP | DEVICE STATE | COMMENT |
|---|---|---|
| 7. | INTERLOCK CLOSED | Initiate SELF-STERILIZE CYCLE Feedback State to User |
| 8. | SELF-STERILIZE CYCLE | Sterilize Active Surface or Part of Active Surface as needed |
| 9. | STAND-BY MODE | Sense Active Surface for re-contamination or possible contamination Feedback State to Device and User |
| | GOTO STEP 4 ABOVE | |

The following is an example of how a Self-Sterilizing device could operate and interact with a user:

1. The device would indicate its current state through the use of an indicator light located near the active surface. The device could provide feedback to the user via other mechanisms, such as small display or a wireless connection to a remote computer.
2. In this example, a colored LED light is used. The light could indicate a red, yellow or green color or indicate all three colors at the same time.
3. When the device is powered on, the device performs a calibration self-test. All indicator lights (red, green & yellow) would be turned on. The self-calibration self-test checks to verify the device power system, sensors, active surface, hardware and software are operating within specifications.
4. After the self-calibration self-test, the device would sense if the active surface is currently being touched by a user or external device. If a user is touching the device, the indicator light would turn yellow and a safety interlock would trigger. The device would go into standby mode. The device will remain in standby mode until it is not being touched.
5. Once the active surface is free, the device will perform the initial self-sterilization cycle. The indicator light would turn red during self-sterilization cycle.
6. Once self-sterilization cycle is complete, the indicator light would turn green.
7. When the user picks up and uses the device or the device senses that it may be contaminated, the indicator light will turn yellow, a safety interlock would trigger and the device would go into standby mode waiting to re-sterilize again.
8. The steps above repeat as needed.

Example 1

Figure 10A:
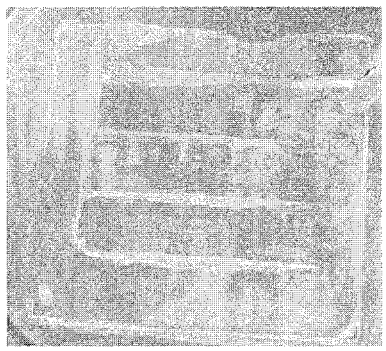
FIGS. 10A-10G show the results of plasma generation on a surface with yeast at 1.5 kV, 14 kHz, at about 20 W, after 1 minute of excitation.
Figure 10A:
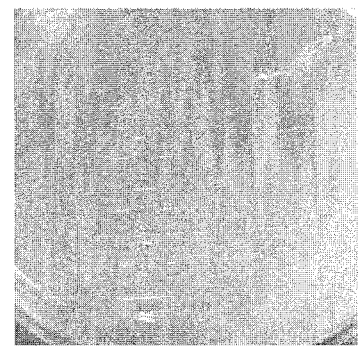
Figure 10B:
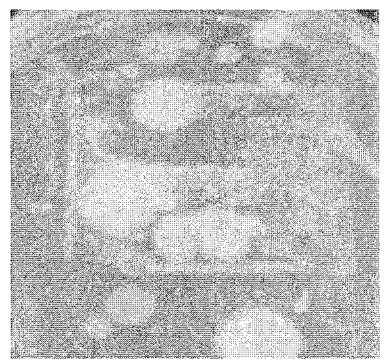
Figure 10B:
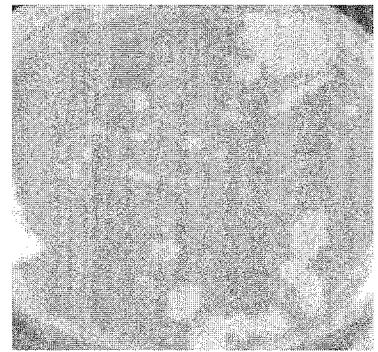
Figure 10C:
Figure 10D:
Figure 10E:
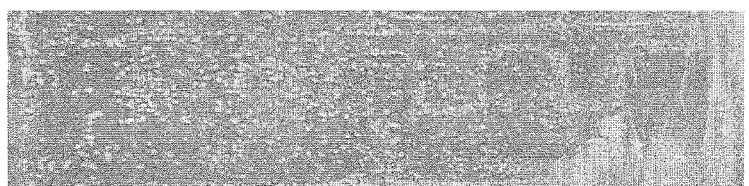
Figure 10F:
Figure 10G:
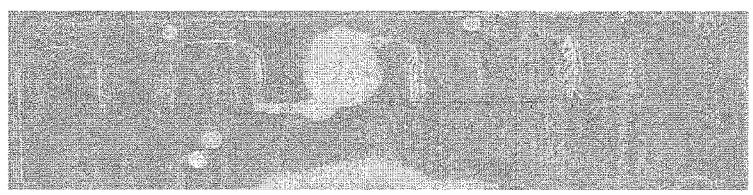
Figure 11:
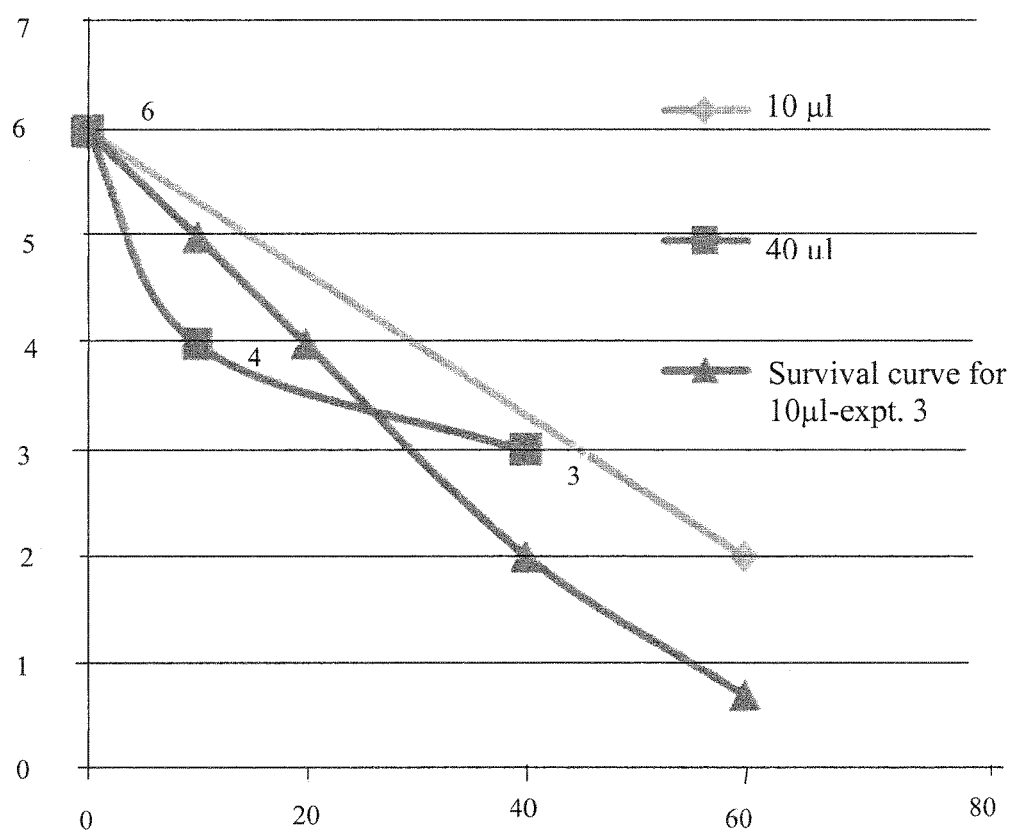
FIG. 11 shows the qualitative nature of the survival curve for yeast on a substrate having 40 μl of yeast solution, the qualitative nature of the survival curve for yeast on a surface having 10 μl of yeast solution, and the qualitative nature of the survival curve for another experiment with respect to yeast on a surface having 10 μl of yeast solution.

This example pertains to a device capable of self-sterilizing a surface of the device. FIGS. 10A-10G show the results of plasma generation on a surface with yeast, at 1.5 kV, 14 kHz, at about 20 W, after various time periods up to 1 minute of excitation. FIG. 10A shows the surface before excitation with 100 µl of yeast solution, where the yeast solution contains $10^9$ spores/ml, and the surface after 1 minute of electrode excitation. FIG. 10B shows the surface before excitation with 10 µl of yeast solution, where the yeast solution contains $10^9$ spores/ml, and the surface after 1 minute of electrode excitation. FIGS. 10C-10G show the surface with 10 µl of yeast solution after 0 seconds, 10 seconds, 20 seconds, 40 seconds, and 60 seconds, respectively, of excitation. FIG. 11 shows the qualitative nature of a survival curve, with time in seconds on the horizontal axis and exponent of number of spores on the vertical axis, showing the qualitative nature of the survival curve (squares) for a surface with 40 µl of yeast solution, the qualitative nature of a survival curve (triangles) for a surface with 10 µl of yeast solution, and the qualitative nature of the survival curve (straight) for a surface with 10 µl of yeast solution.

Various embodiments of the subject invention will now be described.

Embodiment 1 is a device capable of sterilizing or decontaminating at least a portion of a surface of the device, comprising:
a surface; and
a means for generating a plasma that sterilizes or decontaminates at least a portion of the surface.

Embodiment 2 is the device of embodiment 1, wherein the means for generating the plasma comprises:
one or more first electrodes located proximate the surface;
one or more second electrodes located proximate the one or more first electrodes;
a power source for applying a voltage across at least one of the one or more first electrodes and at least one of the one or more second electrodes so as to generate the plasma that sterilizes or decontaminates at least a portion of the surface.

Embodiment 3 is the device of embodiment 1, wherein the means for generating the plasma comprises a means for resistive barrier discharge.

Embodiment 4 is the device of embodiment 1, wherein the means for generating the plasma comprises a means for dielectric barrier discharge.

Embodiment 5 is the device of embodiment 1, wherein the means for generating the plasma comprises a means for producing an atmospheric pressure plasma jet.

Embodiment 6 is the device of embodiment 1, wherein the means for generating the plasma comprises a means for floating electrode dielectric barrier discharge.

Embodiment 7 is the device of embodiment 2, wherein the device is a surgical surface.

Embodiment 8 is the device of embodiment 2, further comprising one or more sensors for detecting potential contamination of the surface or contamination of the surface.

Embodiment 9 is the device of embodiment 8, wherein the at least one of the one or more first electrodes are utilized as at least one of the one or more sensors.

Embodiment 10 is the device of embodiment 9, wherein the at least one first electrode utilized as at least one sensor is at least one capacitive or continuity sensor.

Embodiment 11 is the device of embodiment 8, wherein the one or more sensors are integrated with or located proximate to the one or more first electrodes and/or one or more second electrodes.

Embodiment 12 is the device of embodiment 8, wherein the one or more sensors are positioned at a remote location from the surface.

Embodiment 13 is the device of embodiment 2, wherein the surface is on a laminate material comprising:
a first electrode layer, wherein the first electrode layer incorporates the one or more first electrodes;
a second electrode layer, wherein the second electrode layer incorporates the one or more second electrodes; and
a dielectric layer, wherein the dielectric material of the dielectric layer is located between the at least one of the one or more first electrodes and the at least one of the one or more second electrodes that the voltage is supplied across to produce plasma.

Embodiment 14 is the device of embodiment 2, wherein the at least one first electrode and the at least one second electrode are configured such that the voltage applied across the at least one first electrode and the at least one second electrode results in a dielectric barrier discharge.

Embodiment 15 is the device of embodiment 14, wherein the at least one first electrode and the at least one second electrode are driven as a phase lagged configuration by the power source.

Embodiment 16 is the device of embodiment 2, wherein the surface is curved, wherein the surface is capable of capturing and releasing a sample material, wherein the device allows sterilization of the surface between releasing a first sample material and capturing a second sample material.

Embodiment 17 is the device of embodiment 16, wherein at least a portion of the surface is spherical.

Embodiment 18 is the device of embodiment 2, wherein the device is capable of holding a fluid in a container portion of the device, wherein the surface is a surface of the container portion of the device.

Embodiment 19 is the device of embodiment 13, further comprising: a plurality of apertures extending through the laminate material from a first side to a second side of the laminate material located opposite of the laminate material from the first side, wherein the voltage applied generates a plasma discharge through the plurality of apertures, wherein the surface is a surface of at least one of the plurality of apertures.

Embodiment 20 is the device of embodiment 19, wherein the plasma is ejected outward toward the first side, wherein the plasma ejected toward the first side sterilizes a first outer surface of the first side.

Embodiment 21 is the device of embodiment 19, wherein the plasma discharge is also ejected toward the second side, wherein the plasma ejected toward the second side sterilizes a second outer surface of the second side.

Embodiment 22 is the device of embodiment 2, wherein the surface is located on a first section of the device and the one or more first electrodes and the one or more second electrodes are located on a second section of the device, such that the first section and the second section are moveably connected to each other such that the first section and the second section can transition between a first position and a second position, wherein when the first section and second section are in the first position the one or more first electrodes are located proximate the surface such that applying the voltage across the at least one of the one or more first electrodes and the at least one of the one or more second electrodes generates the plasma that sterilizes and/or decontaminates the surface.

Embodiment 23 is the device of embodiment 2, wherein the surface and the one or more first electrodes are located on a first section of the device and the one or more second electrodes are located on a second section of the device, such that the first section and the second section are moveably connected to each other such that the first section and the second section can transition between a first position and a second position, wherein when the first section and second section are in the first position the one or more first electrodes are located proximate the surface such that applying the voltage across the at least one of the one or more first electrodes and the at least one of the one or more second electrodes generates the plasma that sterilizes and/or decontaminates the surface.

Embodiment 24 is the device of embodiment 22, wherein in the first position the first section is retracted into the second section.

Embodiment 25 is the device of embodiment 24, wherein in the first position the second section is extended out to surround the first section.

Embodiment 26 is the device of embodiment 24, wherein in the first position the second section is extended out into the first section.

Embodiment 27 is the device of embodiment 22, wherein the first section is selected from the group consisting of: needle shafts, hypodermic needles, catheters, tubes, scalpels, knives, implantable devices, syringes, electrodes, surgical instruments, food preparation equipment, drug delivery, and cannulas.

Embodiment 28 is the device of embodiment 2, wherein the device is selected from the group consisting of: needle shafts, hypodermic needles, catheters, tubes, scalpels, knives, implantable devices, syringes, electrodes, surgical instruments, food preparation equipment, drug delivery, and cannulas, balloon catheter, urinary catheter, guiding catheter, ablation device, stent, and implantable device.

Embodiment 29 is the device of embodiment 22, further comprising an interlock switch, wherein the interlock switch controls the transition of the first section and the second section between the first position and the second position.

Embodiment 30 is the device of embodiment 2, wherein the surface and the one or more first electrodes and the one or more second electrodes are located on a first section, wherein the first section can be extended out of a second section of the device such that during generation of the plasma the surface can be moved over at least a portion of an object for sterilization by the plasma, wherein the first section can be retracted back into the second section after sterilization of the object.

Embodiment 31 is the device of embodiment 30, wherein the surface has a cylindrical shape.

Embodiment 32 is the device of embodiment 30, further comprising an interlock switch, wherein the interlock switch controls the extension and retraction of the first section with respect to the second section.

Embodiment 33 is the device of embodiment 2, wherein the surface is an inner surface of the device.

Embodiment 34 is the device of embodiment 33, wherein the surface is cylindrically shaped.

Embodiment 35 is the device of embodiment 33, wherein at least a portion of the surface is concave.

Embodiment 36 is the device of embodiment 33, wherein the device is a beaker or flask.

Embodiment 37 is the device of embodiment 33, wherein the device is a drug delivery port or a pipette.

Embodiment 38 is the device of embodiment 2, wherein the surface is a flexible surface.

Embodiment 39 is the device of embodiment 2, wherein the surface is a woven surface.

Embodiment 40 is the device of embodiment 2, wherein the surface comprises TEFLON™.

Embodiment 41 is the device of embodiment 2, wherein the one or more first electrodes and the one or more second electrodes form a pixilated electrode matrix.

Embodiment 42 is the device of embodiment 41, wherein the pixilated electrodes have a cross-sectional diameter in the range of 1 µm to 100 µm.

Embodiment 43 is the device of embodiment 41, wherein the pixilated electrodes have a cross-sectional diameter in the range of 1 µm to 10 µm.

Embodiment 44 is the device of embodiment 2, wherein the one or more first electrodes comprise a first wire electrode, wherein the one or more second electrodes comprise a second wire electrode, wherein the first wire electrode and the second wire electrode are braided.

Embodiment 45 is the device of embodiment 44, wherein the surface is an outer surface of a tube, wherein the braided first wire electrode and second wire electrode are positioned within a body of the tube.

Embodiment 46 is the device of embodiment 44, wherein the surface is an inner surface of a tube, wherein the braided first wire electrode and second wire electrode are positioned within a body of the tube.

Embodiment 47 is the device of embodiment 46, wherein the tube is at least part of a medical device selected from the group consisting of: a balloon catheter, urinary catheter, guiding catheter, ablation device, an implantable device, and a stent.

Embodiment 48 is the device of embodiment 2, wherein the device is a cutting board.

Embodiment 49 is the device of embodiment 2, wherein the plasma substantially eliminates one or more of the following from the at least a portion of the surface: living organisms, tissue, germs, bacteria, pathogens, biological agents, viruses, metabolically inert agents, pyrons, organic matter, and microorganisms.

Embodiment 50 is the device of embodiment 2, wherein the plasma sterilizes or decontaminates the entire surface.

Embodiment 51 is the device of embodiment 8, wherein the device automatically sterilizes or decontaminates the surface upon the one or more sensors detecting potential contamination of the surface or contamination of the surface.

Embodiment 52 is the device of embodiment 2, further comprising a coating over the one or more first electrodes proximate the surface such that the one or more electrodes are not exposed to the environment.

Embodiment 53 is the device of embodiment 13, further comprising a coating over the one or more first electrodes proximate the surface such that the one or more electrodes are not exposed to the environment.

Embodiment 54 is the device of embodiment 13, wherein the surface of the dielectric coating that would be exposed to the environment is coated with a conductive or semi-conductive material that enhances the generation of the plasma.

Embodiment 55 is the device of embodiment 54, wherein the conductive or semi-conductive material comprises one or more of the following: carbon nanotubes, nanowires, conductive polymers, and nanorods.

Embodiment 56 is the device of embodiment 2, wherein the one or more first electrodes is coated with a conductive or semi-conductive material that enhances the generation of the plasma.

Embodiment 57 is the device of embodiment 56, wherein the conductive or semi-conductive material comprises one or more of the following: carbon nanotubes, nanowires, conductive polymers, and nanorods.

Embodiment 58 is the device of embodiment 13, wherein the one or more first electrodes is coated with a conductive or semi-conductive material that enhances the generation of the plasma.

Embodiment 59 is the device of embodiment 58, wherein the conductive or semi-conductive material comprises one or more of the following: carbon nanotubes, nanowires, conductive polymers, and nanorods.

Embodiment 60 is the device of embodiment 8, wherein the one or more sensors are coated with a conductive or semi-conductive material that enhances the sensitivity and/or specificity of the one or more sensors.

Embodiment 61 is the device of embodiment 60, wherein the conductive or semi-conductive material comprises one or more of the following: carbon nanotubes, nanowires, conductive polymers, and nanorods.

Embodiment 62 is the device of embodiment 52, wherein the coating is coated with a second coating of a conductive or semi-conductive material that enhances the generation of the plasma.

Embodiment 63 is the device of embodiment 62, wherein the conductive or semi-conductive material comprises one or more of the following: carbon nanotubes, nanowires, conductive polymers, and nanorods.

Embodiment 64 is the device of embodiment 8, further comprising a coating over the one or more sensors such that the one or more sensors are not exposed to the environment.

Embodiment 65 is the device of embodiment 64, wherein the coating is coated with a second coating of a conductive or semi-conductive material that enhances the sensitivity and/or specificity of the one or more sensors.

Embodiment 66 is the device of embodiment 65, wherein the conductive or semi-conductive material comprises one or more of the following: carbon nanotubes, nanowires, conductive polymers, and nanorods.

Embodiment 67 is the device of embodiment 41, further comprising one or more sensors for detecting potential contamination of the surface or contamination of the surface.

Embodiment 68 is the device of embodiment 67, wherein the device automatically sterilizes or decontaminates the surface upon the one or more sensors detecting potential contamination of the surface or contamination of the surface.

Embodiment 69 is the device of embodiment 68, wherein the device is capable of sterilizing or decontaminating only portions of the surface that the one or more sensors detect potential contamination of the surface or contamination of the surface by exciting pixilated electrodes in the portions of the surface that the potential contamination of the surface or contamination of the surface occurs.

Embodiment 70 is the device of embodiment 2, wherein the device is capable of sterilizing or decontaminating one or more objects positioned on the surface.

Embodiment 71 is the device of embodiment 70, wherein the device automatically sterilizes the object when the objects are positioned on the surface.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] Kanda, N., M. Kogoma, H. Jinno, H. Uchiyama and S. Okazaki, Proc. 10th Symp. On Plasma Chem., Vol. 3, Paper no. 3.2-20 (1991).
[2] Roth, J. R., Physics of Plasmas, 10 (5), 2117 (2003).
[3] S. Roy, K. P. Singh, H. Kumar, D. Gaitonde, and M. Visbal, Effective discharge dynamics for plasma actuators, AIAA-2006-0374, 44th Aerospace Sciences Meeting and Exhibit, 9-12 Jan., 2006.
[4] S. Roy, Flow actuation using radio frequency in partially-ionized collisional plasmas, Applied Physics Letters, 86 (10) 101502 (2005).

[5] M. Heisel, W. Neffl, O. Franken, P. Muranyi and J. Wunderlich, Sterilization of Polymer Foils with Dielectric Barrier Discharges at Atmospheric Pressure, Plasmas and Polymers, 9 (1) 23-33 (2004).

[6] M. Tanino, W. Xilu, K. Takashima, S. Katsura and A. Mizuno, Sterilization using dielectric barrier discharge at atmospheric pressure, Industry Applications Conference, 2005. Fortieth IAS Annual Meeting. Vol. 2, 784-788 (2005).

[7] M. Moisan, J. Barbeau, S. Moreau, J. Pelletier, M. Tabrizian and L'H. Yahia, Low-temperature sterilization using gas plasmas: a review of the experiments and an analysis of the inactivation mechanisms, International Journal of Pharmaceutics, 226, 1-21 (2001).

[8] Fridman G., Peddinghaus L., Vinovrski T., Jah A., Fridman A., Balasubramanian M., Gutsol A., Friedman G., "Use of Non-Thermal Atmospheric Pressure Plasma Discharge for Coagulation and Sterilization of Surface Wounds", 32nd IEEE International Conference on Plasma Science, Jun. 20-23, 2005, Monterey, Calif., IEEE Conference Record—Abstracts, p. 257.

[9] G. Fridman, A. Shereshevsky, M. Peddinghaus, A. Gutsol, V. Vasilets, A. Brooks, M. Balasubramanian, G. Friedman, and A. Fridman, Drexel University, Philadelphia, Pa. "Bio-Medical Applications of Non-Thermal Atmospheric Pressure Plasma" AIAA-2006-2902 37th AIAA Plasma dynamics and Lasers Conference, San Francisco, Calif., Jun. 5-8, 2006.

[10] Andrew Rinzler, et al., "Transparent electrodes from single wall carbon nanotubes." U.S. Pat. No. 7,261,852. 28 Aug. 2007.

[11] F. Ren, ZnO Nanowires for Sensing and Device Applications, 212$^{th}$ ECS Meeting, Oct. 7-12, 2007, Washington, D.C.

[12] S. Kanazawa, M. Kogoma, T. Moriwaki, and S. Okazaki, *J. Appl. Phys. D: Appl. Phys.* 21 (1988) 838.

[13] M. Laroussi, I. Alexeff, J. P. Richardson, and F. F. Dyer, *IEEE Trans. Plasma Sci.* 30 (2002) 158.

[14] A. Scutze, J. Y. Jeong, S. E. Babyan, J. park, G. S. Selwyn, and R. F. Hicks, *IEEE Trans. Plasma Sci.* 26 (1998) 1685.

The invention claimed is:

1. A method of sterilizing at least a portion of a surface of a device, comprising:
    providing a device with at least a portion of a surface of the device exposed to an environment of interest; and
    producing a plasma proximate the entire at least the portion of the surface of the device for a duration sufficient to sterilize the entire at least the portion of the surface of the device,
    wherein the entire at least the portion of the surface of the device is sterilized via the plasma,
    wherein producing the plasma proximate the entire at least the portion of the surface of the device comprises:
        providing a plurality of first electrodes located proximate the at least the portion of the surface of the device,
        wherein the plurality of first electrodes are incorporated into the at least the portion of the surface of the device;
        providing one or more second electrodes located proximate the plurality of first electrodes;
        providing a dielectric material,
        wherein the dielectric material is located between the plurality of first electrodes and the one or more second electrodes; and
        applying at least one voltage across the plurality of first electrodes and the one or more second electrodes such that:
            (i) for each first electrode of the plurality of first electrodes, one voltage of the at least one voltage is applied across the each first electrode of the plurality of first electrodes and at least one second electrode of the one or more second electrodes with the dielectric material located between the each first electrode of the plurality of first electrodes and the at least one second electrode of the one or more second electrodes; and
            (ii) for each second electrode of the one or more second electrodes, one voltage of the at least one voltage is applied across at least one first electrode of the plurality of first electrodes and the each second electrode of the one or more second electrodes with the dielectric material located between the at least one first electrode of the plurality of first electrodes and the each second electrode of the one or more second electrodes,
    such that applying the at least one voltage across the plurality of first electrodes and the one or more second electrodes results in a corresponding at least one dielectric barrier discharge, and
    wherein the at least one dielectric barrier discharge produces the plasma proximate the entire at least the portion of the surface of the device for a duration sufficient to sterilize the entire at least the portion of the surface of the device.

2. The method according to claim 1, further comprising: providing one or more sensors for detecting potential contamination of the at least the portion of the surface of the device or contamination of the at least the portion of the surface of the device.

3. The method according to claim 2, further comprising: automatically producing the plasma proximate the entire at least the portion of the surface of the device upon the one or more sensors detecting potential contamination of the at least the portion of the surface of the device or the one or more sensors detecting contamination of the at least the portion of the surface of the device.

4. The method according to claim 2, wherein the one or more sensors are coated with a conductive or semi-conductive material that enhances the sensitivity and/or specificity of the one or more sensors.

5. The method according to claim 4, wherein the conductive or semi-conductive material comprises one or more of the following: carbon nanotubes, nanowires, conductive polymers, and nanorods.

6. The method according to claim 2, further comprising: a coating over the one or more sensors such that the one or more sensors are not exposed to the environment of interest.

7. The method according to claim 6, wherein the coating is coated with a second coating of a conductive or semi-conductive material that enhances the sensitivity and/or specificity of the one or more sensors.

8. The method according to claim 7, wherein the conductive or semi-conductive material comprises one or more of the following: carbon nanotubes, nanowires, conductive polymers, and nanorods.

9. The method according to claim 1, further comprising:
exposing the at least the portion of the surface of the device to an environment having nonsterile matter contaminants,
wherein producing the plasma proximate the entire at least the portion of the surface of the device comprises producing the plasma proximate the entire at least the portion of the surface of the device after exposing the at least the portion of the surface of the device to the environment having nonsterile matter contaminants.

10. The method according to claim 1,
wherein the at least the portion of the surface of the device is at least the portion of a surgical surface of the device.

11. The method according to claim 1,
wherein the at least the portion of the surface of the device is a corresponding at least a portion of a first surface of a corresponding at least a portion of a laminate material, and
wherein the at least the portion of the laminate material comprises:
a first electrode layer,
wherein the first electrode layer comprises the plurality of first electrodes;
a second electrode layer,
wherein the second electrode layer comprises the one or more second electrodes; and
a dielectric layer,
wherein the dielectric layer comprises the dielectric material.

12. The method according to claim 11,
wherein the plurality of first electrodes proximate the at least the portion of the surface of the device have a coating such that the plurality of first electrodes are not exposed to the environment of interest.

13. The method according to claim 11,
wherein a portion of a surface of the dielectric layer that would be exposed to the environment of interest is coated with a conductive or semi-conductive material such that the portion of the surface of the dielectric layer is not exposed to the environment of interest, and
wherein the conductive or semi-conductive material enhances the generation of the plasma.

14. The method according to claim 13,
wherein the conductive or semi-conductive material comprises one or more of the following:
carbon nanotubes, nanowires, conductive polymers, and nanorods.

15. The method according to claim 11,
wherein the plurality of first electrodes are coated with a conductive or semi-conductive material that enhances the generation of the plasma.

16. The method according to claim 15,
wherein the conductive or semi-conductive material comprises one or more of the following:
carbon nanotubes, nanowires, conductive polymers, and nanorods.

17. The method according to claim 1,
wherein the device is configured to hold a fluid in a container portion of the device, and
wherein the at least the portion of the surface of the device is at least a portion of a surface of the container portion of the device.

18. The method according to claim 1,
wherein the at least the portion of the surface of the device and the plurality of first electrodes are located on a first section of the device, and the one or more second electrodes are located on a second section of the device,
wherein the first section of the device and the second section of the device are moveably connected to each other such that the first section of the device and the second section of the device can transition between a first position and a second position,
wherein when the first section of the device and the second section of the device are in the first position the one or more second electrodes are located proximate the plurality of first electrodes such that applying the at least one voltage across the plurality of first electrodes and the one or more second electrodes generates the plasma that sterilizes the entire at least the portion of the surface of the device, and
wherein when the first section of the device and the second section of the device are in the second position the one or more second electrodes are not located proximate the plurality of first electrodes such that applying the at least one voltage across the plurality of first electrodes and the one or more second electrodes does not generate the plasma that sterilizes the entire at least the portion of the surface of the device.

19. The method according to claim 18,
wherein when the first section of the device and second section of the device are in the first position, the second section of the device is extended out to surround the first section of the device.

20. The method according to claim 18,
wherein when the first section of the device and second section of the device are in the first position, the second section of the device is extended out into the first section of the device.

21. The method according to claim 1,
wherein the device is selected from the group consisting of:
a needle shaft, a hypodermic needle, a catheter, a scalpel, a knife, a syringe, a surgical instrument, food preparation equipment, a drug delivery device, a cannula, a balloon catheter, a urinary catheter, a guiding catheter, an ablation device, a stent, and an implantable device.

22. The method according to claim 1,
wherein the at least the portion of the surface of the device, the plurality of first electrodes, and the one or more second electrodes are located on a first section of the device,
wherein the first section of the device can be extended out of a second section of the device such that during generation of the plasma the at least the portion of the surface of the device can be moved over at least a portion of an object for sterilization of the at least the portion of the object via the plasma, and
wherein the first section of the device can be retracted back into the second section of the device after sterilization of the at least the portion of the object via the plasma.

23. The method according to claim 1,
wherein the at least the portion of the surface of the device is at least a portion of an inner surface of the device.

24. The method according to claim 23,
wherein the at least the portion of the surface of the device is concave.

25. The method according to claim 23,
wherein the device is a beaker or flask.

26. The method according to claim 23,
wherein the device is a drug delivery port or a pipette.

27. The method according to claim 1,
wherein the at least the portion of the surface of the device is a flexible at least the portion of the surface of the device.

28. The method according to claim 1,
wherein the plurality of first electrodes comprise a pixel shape electrode matrix such that each first electrode of the plurality of first electrodes is a pixel electrode of the pixel shape electrode matrix.

29. The method according to claim 28,
wherein each first electrode of the pixel shape electrode matrix has a cross-sectional diameter in the range of 1 μm to 100 μm.

30. The method according to claim 28,
wherein each pixel electrode of the pixel shape electrode matrix has a cross-sectional diameter in the range of 1 μm to 10 μm.

31. The method according to claim 28, further comprising:
one or more sensors,
wherein the one or more sensors detect potential contamination of the at least the portion of the surface of the device or the one or more sensors detect contamination of the at least the portion of the surface of the device.

32. The method according to claim 31, further comprising:
automatically producing the plasma proximate the entire at least the portion of the surface of the device for a duration sufficient to sterilize the entire at least the portion of the surface of the device upon the one or more sensors detecting potential contamination of the at least the portion of the surface of the device or the one or more sensors detecting contamination of the at least the portion of the surface of the device.

33. The method according to claim 31, further comprising:
automatically producing the plasma proximate only sub portions of the at least the portion of the surface of the device that the one or more sensors detect potential contamination thereof or that the one or more sensors detect contamination thereof, by exciting pixel electrodes in the sub portions of the at least the portion of the surface of the device that the one or more sensors detect potential contamination thereof or that the one or more sensors detect contamination thereof.

34. The method according to claim 1,
wherein the plurality of first electrodes comprise a first wire electrode,
wherein the one or more second electrodes comprise a second wire electrode, and
wherein the first wire electrode and the second wire electrode are braided.

35. The device according to claim 34,
wherein the at least the portion of the surface of the device is at least the portion of an outer surface of a tube, and
wherein the braided first wire electrode and second wire electrode are positioned outside a body of the tube.

36. The method according to claim 34,
wherein the at least the portion of the surface of the device is at least a portion of an inner surface of a tube, and
wherein the braided first wire electrode and second wire electrode are positioned inside a body of the tube.

37. The method according to claim 1,
wherein the device is a cutting board.

38. The method according to claim 1,
wherein the plasma substantially eliminates one or more of the following from the entire at least the portion of the surface:
living organisms, tissue, germs, bacteria, pathogens, biological agents, viruses, metabolically inert agents, prions, organic matter, and microorganisms.

39. The method according to claim 1,
wherein the plasma sterilizes the entire surface of the device.

40. The method according to claim 39,
wherein providing the device with the at least the portion of the surface of the device exposed to the environment of interest comprises providing the device with the entire surface of the device exposed to the environment of interest.

41. The method according to claim 39,
wherein the entire surface of the device is solid.

42. The method according to claim 1,
wherein the plurality of first electrodes proximate the at least the portion of the surface of the device have a coating such that the plurality of first electrodes are not exposed to the environment of interest.

43. The method according to claim 42,
wherein the coating is coated with a second coating of a conductive or semi-conductive material that enhances the generation of the plasma.

44. The method according to claim 43,
wherein the conductive or semi-conductive material comprises one or more of the following:
carbon nanotubes, nanowires, conductive polymers, and nanorods.

45. The method according to claim 1,
wherein the plurality of first electrodes are coated with a conductive or semi-conductive material that enhances the generation of the plasma.

46. The method according to claim 45,
wherein the conductive or semi-conductive material comprises one or more of the following:
carbon nanotubes, nanowires, conductive polymers, and nanorods.

47. The method according to claim 1, further comprising:
positioning one or more objects on the at least the portion of the surface of the device; and
producing the plasma proximate the at least the portion of the surface of the device for a duration sufficient to sterilize the one or more objects positioned on the at least the portion of the surface of the device,
wherein the one or more objects positioned on the at least the portion of the surface of the device are sterilized via the plasma.

48. The method according to claim 47,
wherein the device automatically produces the plasma proximate the at least the portion of the surface of the device for a duration sufficient to sterilize the one or more objects positioned on the at least the portion of the surface of the device when the one or more objects are positioned on the at least the portion of the surface of the device.

49. The method according to claim 1,
wherein the at least the portion of the surface of the device, the plurality of first electrodes, and the one or more second electrodes are located on a first section of the device,
wherein the first section of the device is moveably connected to a second section of the device, and wherein the first section of the device is configured to be extended out of the second section of the device.

50. The method according to claim 1,
wherein applying at least one voltage across the plurality of first electrodes and the one or more second electrodes so as to produce the plasma comprises applying a first voltage directly to the plurality of first electrodes and applying a second voltage directly to the one or more second electrodes, and
wherein a difference between the first voltage and the second voltage is the at least one voltage.

51. The method according to claim 1,
wherein the plurality of first electrodes is embedded in the at least the portion of the surface of the device.

52. The method according to claim 51,
wherein the dielectric material is positioned between the plurality of first electrodes and the environment of interest the at least the portion of the surface of the device is exposed to.

53. The method according to claim 1,
wherein applying the at least one voltage across the plurality of first electrodes and the one or more second electrodes comprises applying at least one pulsing a.c. or d.c. voltage to the plurality of first electrodes, and
wherein the one or more second electrodes are grounded.

54. The method according to claim 1,
wherein providing the device with the at least the portion of the surface of the device exposed to the environment of interest comprises providing the device into a surrounding environment such that the device is exposed to the surrounding environment, and
wherein the environment of interest is the surrounding environment.

55. The method according to claim 1,
wherein the plurality of first electrodes are positioned on the at least the portion of the surface of the device so as to be attached to the at least the portion of the surface of the device.

56. The method according to claim 1,
wherein the plasma sterilizes the entire at least the portion of the surface of the device by the plasma contacting the entire at least the portion of the surface of the device for a duration sufficient to sterilize the entire at least the portion of the surface of the device.

57. The method according to claim 1,
wherein the plasma sterilizes the entire surface of the device by the plasma contacting the entire surface of the device for a duration sufficient to sterilize the entire surface of the device.

58. The method according to claim 1,
wherein the at least the portion of the surface is non-permeable.

59. A method of sterilizing at least a portion of a surface of a device, comprising:
providing a device with at least a portion of a surface of the device exposed to an environment of interest; and
producing a plasma proximate the entire at least the portion of the surface of the device for a duration sufficient to sterilize the entire at least the portion of the surface of the device,
wherein the entire at least the portion of the surface of the device is sterilized via the plasma,
wherein producing the plasma proximate the entire at least the portion of the surface of the device comprises:
providing a plurality of first electrodes located proximate the at least the portion of the surface of the device,
wherein the plurality of first electrodes are incorporated into the at least the portion of the surface of the device;
providing one or more second electrodes located proximate the plurality of first electrodes;
providing a dielectric material,
wherein the dielectric material is located between the plurality of first electrodes and the one or more second electrodes; and
applying at least one voltage across the plurality of first electrodes and the one or more second electrodes such that:
(i) for each first electrode of the plurality of first electrodes, one voltage of the at least one voltage is applied across the each first electrode of the plurality of first electrodes and at least one second electrode of the one or more second electrodes with the dielectric material located between the each first electrode of the plurality of first electrodes and the at least one second electrode of the one or more second electrodes; and
(ii) for each second electrode of the one or more second electrodes, one voltage of the at least one voltage is applied across at least one first electrode of the plurality of first electrodes and the each second electrode of the one or more second electrodes with the dielectric material located between the at least one first electrode of the plurality of first electrodes and the each second electrode of the one or more second electrodes,
such that applying the at least one voltage across the plurality of first electrodes and the one or more second electrodes results in a corresponding at least one dielectric barrier discharge, and
wherein the at least one dielectric barrier discharge produces the plasma proximate the entire at least the portion of the surface of the device for a duration sufficient to sterilize the entire at least the portion of the surface of the device,
wherein the plurality of first electrodes are not exposed to the environment of interest, and
wherein the one or more second electrodes are not exposed to the environment of interest.

60. The method according to claim 59,
wherein the at least the portion of the surface of the device is a corresponding at least a the portion of a first surface of a corresponding at least the portion of a laminate material,
wherein the at least the portion of the laminate material comprises:
a first electrode layer,
wherein the first electrode layer comprises the plurality of first electrodes;
a second electrode layer,
wherein the second electrode layer comprises the one or more second electrodes; and
a dielectric layer,
wherein the dielectric layer comprises the dielectric material.

61. The method according to claim 60,
wherein the at least the portion of the laminate material further comprises:
a plurality of bores extending through the at least the portion of the laminate material from the at least the portion of the first surface of the at least the portion of the laminate material to a corresponding at least a portion of a second surface of the at least the portion of the laminate material located opposite of the at least the portion of the first surface of the at least the portion of the laminate material, and wherein the at least one voltage applied across the plurality of first electrodes and the one or more second electrodes produces the plasma proximate the at least the portion of the first surface of the at least the portion of the laminate material such that a corresponding plurality of dielectric barrier discharges of the at least one dielectric barrier discharge is produced through the plurality of bores.

62. The method according to claim 61, wherein the plurality of dielectric barrier discharges of the at least one dielectric barrier discharge produced through the plurality of bores is ejected outward from the at least the portion of the first surface of the at least the portion of the laminate material, and wherein the the plurality of dielectric barrier discharges of the at least one dielectric barrier discharge produced through the plurality of bores ejected outward from the at least the portion of the first surface of the at least the portion of the laminate material sterilizes the entire at least the portion of the first surface of the at least the portion of the laminate material.

63. The method according to claim 62, wherein the plurality of dielectric barrier discharges of the at least one dielectric barrier discharge produced through the plurality of bores is also ejected from the at least the portion of the second surface of the at least the portion of the laminate material, and wherein the plurality of dielectric barrier discharges of the at least one dielectric barrier discharge produced through the plurality of bores ejected from the at least the portion of the second surface of the at least the portion of the laminate material sterilizes the entire at least a the portion of the second surface of the at least the portion of the laminate material.

64. The method according to claim 59, wherein the at least the portion of the surface of the device is a woven at least the portion of the surface of the device.

65. The method according to claim 59, wherein the plurality of first electrodes comprise a first wire electrode, wherein the one or more second electrodes comprise a second wire electrode, and wherein the first wire electrode and the second wire electrode are braided.

66. The device according to claim 65, wherein the at least the portion of the surface of the device is at least a portion of an outer surface of a tube, and wherein the braided first wire electrode and second wire electrode are positioned within outside a body of the tube.

67. The method according to claim 65, wherein the at least the portion of the surface of the device is at least a portion of an inner surface of a tube, and wherein the braided first wire electrode and second wire electrode are positioned within inside a body of the tube.

68. The method according to claim 59, wherein the plasma sterilizes the entire surface of the device.

69. The method according to claim 68, wherein providing the device with the at least the portion of the surface of the device exposed to the environment of interest comprises providing the device with the entire surface of the device exposed to the environment of interest.

70. The method according to claim 59, wherein applying at least one voltage across the plurality of first electrodes and the one or more second electrodes so as to produce the plasma comprises applying a first voltage directly to the plurality of first electrodes and applying a second voltage directly to the one or more second electrodes, and wherein a difference between the first voltage and the second voltage is the at least one voltage.

71. The method according to claim 59, wherein the plurality of first electrodes are embedded in the at least the portion of the surface of the device.

72. The method according to claim 59, wherein applying the at least one voltage across the plurality of first electrodes and the one or more second electrodes comprises applying at least one pulsing a.c. or d.c. voltage to the plurality of first electrodes, and wherein the one or more second electrodes are grounded.

73. The method according to claim 59, wherein providing the device with the at least the portion of the surface of the device exposed to the environment of interest comprises providing the device into a surrounding environment such that the device is exposed to the surrounding environment, and wherein the environment of interest is the surrounding environment.

74. The method according to claim 59, wherein the plurality of first electrodes are positioned on the at least the portion of the surface of the device so as to be attached to the at least the portion of the surface of the device.

* * * * *

UNITED STATES PATENT AND TRADEMARK OFFICE
CERTIFICATE OF CORRECTION

| | | |
|---|---|---|
| PATENT NO. | : 9,757,487 B2 | Page 1 of 1 |
| APPLICATION NO. | : 12/743625 | |
| DATED | : September 12, 2017 | |
| INVENTOR(S) | : Subrata Roy and Karl R. Zawoy | |

It is certified that error appears in the above-identified patent and that said Letters Patent is hereby corrected as shown below:

In the Specification

Column 2,
Line 3, "and inns" should read --and rms--.

Signed and Sealed this
Twenty-sixth Day of June, 2018

Andrei Iancu
*Director of the United States Patent and Trademark Office*